(12) United States Patent
Kobayashi

(10) Patent No.: US 7,414,145 B2
(45) Date of Patent: Aug. 19, 2008

(54) METHOD OF ENANTIOSELECTIVE NUCLEOPHILIC ADDITION REACTION OF ENAMIDE TO CARBONYL GROUP AND SYNTHESIS METHOD OF OPTICALLY ACTIVE α-HYDROXY-γ-KETO ACID ESTER AND HYDROXYDIKETONE

(75) Inventor: Shu Kobayashi, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 10/587,078

(22) PCT Filed: Jan. 24, 2005

(86) PCT No.: PCT/JP2005/001281

§ 371 (c)(1),
(2), (4) Date: Oct. 20, 2006

(87) PCT Pub. No.: WO2005/070864

PCT Pub. Date: Aug. 4, 2005

(65) Prior Publication Data

US 2007/0073087 A1    Mar. 29, 2007

(30) Foreign Application Priority Data

Jan. 23, 2004    (JP) ............................... 2004-016408
Aug. 27, 2004    (JP) ............................... 2004-249251

(51) Int. Cl.
*C07C 271/00*    (2006.01)
*C07C 269/00*    (2006.01)
*C07D 207/00*    (2006.01)
*C07D 307/00*    (2006.01)

(52) U.S. Cl. ........................... 560/29; 560/32; 560/157; 560/160; 560/163; 560/336; 560/346; 548/400; 548/543; 549/295; 549/313

(58) Field of Classification Search ................. 568/412; 560/29, 32, 157, 160, 163, 336, 346; 548/400, 548/543; 549/295, 313
See application file for complete search history.

(56) References Cited

FOREIGN PATENT DOCUMENTS

JP    2003-260363    9/2003
JP    2003-260366    9/2003

OTHER PUBLICATIONS

Ryosuke Matsubara, Yoshitaka Nakamura and Shu kobayashi Angew. Chem. Int. Ed. 2004, 43, 3258-3260.*
Ryosuke Matsubara et al., "Copper(II)-Catalyzed Highly Enantioselective Addition of Enamides to Imines: The Use of Enamides as Nucleophiles in Asymmetric Catalysis", Angew. Chem. Int. Ed., 43, pp. 1679-1681, 2004.
Yoshitaka Nakamura et al. "Catalytic, Asymmetric Mannich-Type Reactions of α-Imino Esters Bearing Readily Removable Substituents on Nitrogen", Organic Letters, vol. 5, No. 14, pp. 2481-2484, 2003.
Shü Kobayashi et al., "Catalytic, Asymmetric Mannich-Type Reactions of N-Acylimino Esters for Direct Formation of N-Acylated Amino Acid Derivatives. Efficient Synthesis of a Novel Inhibitor of Ceramide Trafficking, HPA-12" Organic Letters, vol. 4, No. 1, pp. 143-145, 2002.
Shü Kobayashi et al., "Catalytic Asymmetric Synthesis of α-Amino Phosphonates Using Enantioselective Carbon Carbon Bond-Forming Reactions", J. Am. Chem. Soc., 126, pp. 6558-6559, 2004.
Ryosuke Matsubara et al., "Highly Diastereo- and Enantioselective Reactions of Enecarbamates with Ethyl Glyoxylate to Give Optically Active *syn* and *anti* α-Alkyl-β-Hydroxy Imines and Ketones", Angew. Chem. Int. Ed., 43, 3258-3260, 2004.
Ryosuke Matsubara et al., "Highly diastereo- and enantioselective reactions of enecarbamates with an aldehyde", Tetrahedron, 60, pp. 9769-9784, 2004.
Ryosuke Matsubara et al., "Development of Catalytic Asymmetric Reactions Using Enamides as Nucleophiles", The Chemical Society of Japan, p. 1220, Mar. 11, 2004.

* cited by examiner

*Primary Examiner*—P. Nazario Gonzalez
(74) *Attorney, Agent, or Firm*—Wenderoth, Lind & Ponack, L.L.P.

(57) ABSTRACT

A method of an enantioselective nucleophilic addition reaction to carbonyl, which enables an asymmetric synthesis of an optically active α-hydroxy-γ-keto acid ester, an optically active α-hydroxy-γ-amino acid ester, hydroxydiketone compounds, etc. being useful as a raw material or synthesis intermediate for producing a pharmaceutical preparation, an agricultural chemical, a fragrance, a functional polymer or the like. In this method, the nucleophilic addition reaction of enamide compound accompanied by hydroxyl (—OH) formation to carbonyl is carried out in the presence of a chiral catalyst with copper or nickel.

12 Claims, No Drawings

METHOD OF ENANTIOSELECTIVE NUCLEOPHILIC ADDITION REACTION OF ENAMIDE TO CARBONYL GROUP AND SYNTHESIS METHOD OF OPTICALLY ACTIVE α-HYDROXY-γ-KETO ACID ESTER AND HYDROXYDIKETONE

TECHNICAL FIELD

The present invention relates to a method of an enantioselective nucleophilic addition reaction of enamide to a carbonyl group which enables an asymmetric synthesis of an optically active compound which is useful as a raw material or a synthesis intermediate for producing a pharmaceutical preparation, an agricultural chemical, a fragrance, a functional polymer or the like and, as an application thereof, a synthesis method of an optically active α-hydroxy-γ-keto acid ester, hydroxydiketone or the like.

BACKGROUND ART

Conventionally, a method of a nucleophilic addition reaction to an aldehyde group of an aldehyde compound or an imino group of an imine compound derived from the aldehyde compound has been studied and, in recent years, this nucleophilic addition reaction has drawn attention as a measure for efficiently and asymmetrically synthesizing an amino acid derivative, a hydroxycarboxylic acid or the like as a raw material or a synthesis intermediate for producing a pharmaceutical preparation, an agricultural chemical, a fragrance, a functional polymer or the like.

Under these circumstances, the present inventors have developed and disclosed a method for synthesizing an N-acylated amino acid derivative by a nucleophilic addition reaction to an N-acylimino ester compound by using a polymer-carrying catalyst (Journal of Combinatorial Chemistry, 2001, Vol. 3, No. 5, 401 to 403) and, further, a method for enantioselectively synthesizing these compounds by using a chiral copper catalyst (Org. Lett. Vol. 4, No. 1, 2002, 143 to 145; J. Am. Chem. Soc. Vol. 125, No. 9, 2003, 2507 to 2515).

However, the nucleophilic addition reaction on which the present inventors have studied is limited to such nucleophilic reactants as a silyl enol ether and an alkyl vinyl ether and, accordingly, a subject to which the nucleophilic addition reaction is applied and such application thereof have inevitably been restricted.

Then, under these circumstances, the present invention has an object of providing a method of an enantioselective nucleophilic addition reaction to a carbonyl group which enables an asymmetric synthesis of an α-hydroxy-γ-keto acid compound, an α-hydroxy-γ-amino acid compound or the like which is useful as a raw material or a synthesis intermediate for producing a pharmaceutical preparation, an agricultural chemical, a fragrance, a functional polymer or the like and, further, as an application thereof, a novel synthesis method of the α-hydroxy-γ-keto acid ester or the like.

DISCLOSURE OF INVENTION

In order to solve these problems, according to a first aspect of the present invention, there is provided a method of an enantioselective nucleophilic addition reaction of enamide which is a method of a nucleophilic addition reaction of an enamide compound accompanied by generation of a hydroxyl group (—OH) to a carbonyl group and which is characterized by allowing the reaction to be performed in the presence of a chiral catalyst containing copper or nickel.

Then, with reference to the above-described method, according to a second aspect of the invention, there is provided the method of the enantioselective nucleophilic addition reaction of enamide which is characterized in that the chiral catalyst is constituted by a copper compound or a nickel compound which is a salt of an organic or inorganic acid or a complex or composite of the salt, and a chiral diamine ligand and, according to a third aspect of the invention, there is provided the method of the enantioselective nucleophilic addition reaction of enamide which is characterized in that the chiral diamine ligand has an ethylene diamine structure as a portion thereof.

Further, according to a fourth aspect of the invention, with reference to the above-described method, there is provided the method of the enantioselective nucleophilic addition reaction of enamide which is characterized in that a nucleophilic addition reaction of an enamide compound accompanied by generation of a hydroxyl group (—OH) to a carbonyl group is performed on a compound having a carbonyl group represented by the following formula:

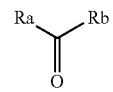

(wherein Ra represents a hydrocarbon group which may have a substituent, $R^0$—CO— or $R^0$—O—CO—, wherein $R^0$ represents a hydrocarbon group which may have a substituent; and Rb represents a hydrogen atom or a hydrocarbon group which may have a substituent).

According to a fifth aspect of the invention, there is provided the method of the enantioselective nucleophilic addition reaction of enamide which is characterized in that the compound having the carbonyl group is a glyoxylic acid ester and, according to a sixth aspect of the invention, there is provided the method which is characterized in that an aldehyde compound is a glyoxylic acid ester represented by the following formula (1):

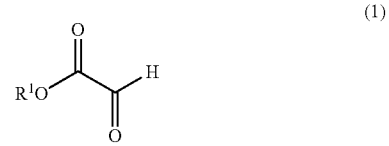

(wherein $R^1$ represents a hydrocarbon group which may have a substituent; and the enamide compound is represented by the following formula (2):

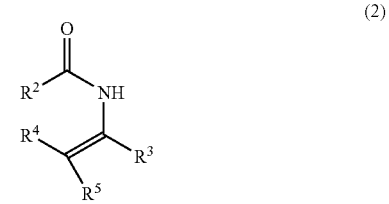

(wherein $R^2$ represents a hydrocarbon group which may have a substituent or a hydrocarbon group which may have a substituent to be bonded via an oxygen atom;

$R^3$ represents a hydrocarbon group which may have a substituent;

$R^4$ and $R^5$ may be same with or different from each other and each represent a hydrogen atom or a hydrocarbon group which may have a substituent, wherein at least one of them represents a hydrogen atom; and $R^3$ may form a ring by being bonded with $R^4$ or $R^5$).

According to a seventh aspect of the invention, there is provided a method for synthesizing an optically active α-hydroxy-γ-keto acid ester which is characterized in that, after the above-described nucleophilic addition reaction, an acid treatment is performed, to thereby generate a compound represented by at least one of the following formulae (3):

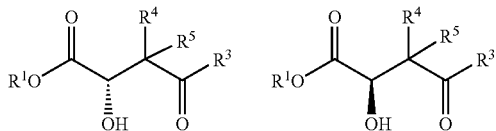

(3)

(wherein $R^1$, $R^3$, $R^4$ and $R^5$ each represent same article as described above) and, according to an eighth aspect of the invention, there is provided a method for synthesizing an optically active α-hydroxy-γ-amino acid ester which is characterized in that, after the above-described nucleophilic addition reactions a reduction treatment is performed, to thereby generate a compound represented by at least one of the following formulae (4):

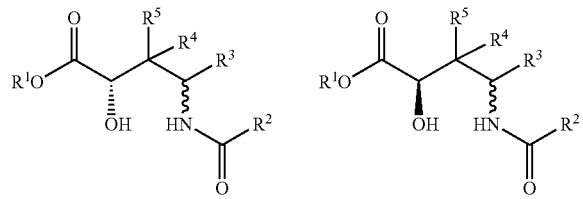

(4)

(wherein $R^1$, $R^2$, $R^3$, $R^4$ and $R^5$ each represent same article as described above) and, further, according to a ninth aspect of the invention, there is provided a method for synthesizing any one of optically active α-hydroxy-γ-lactams which is characterized in that, after a substituent ($R^2CO$—) on a γ-amino group of the thus-synthesized optically active α-hydroxy-γ-amino acid ester is removed, a cyclization reaction is performed, to thereby generate a compound represented by at least one of the following formulae (5):

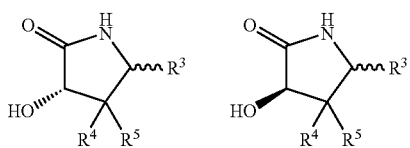

(5)

(wherein $R^3$, $R^4$ and $R^5$ each represent same article as described above).

Still further, according to a tenth aspect of the invention, there is provided a method for synthesizing any one of optically active α-hydroxy-γ-lactones which is characterized in that the optically active α-hydroxy-γ-keto acid ester synthesized by the above-described seventh aspect of the invention is subjected to a reduction reaction and, subsequently, to a cyclization reaction, to thereby generate a compound represented by at least one of the following formulae (6):

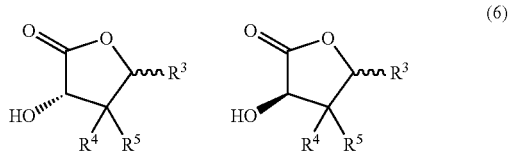

(6)

(wherein $R^3$, $R^4$ and $R^5$ each represent same article as described above).

Then, according to an eleventh aspect of the invention, there is provided a method of an enantioselective nucleophilic addition reaction of enamide which is the enantioselective nucleophilic addition reaction of enamide according to the fourth aspect of the invention and which is characterized in that the compound having the carbonyl group is a diketone compound represented by the following formulae (7):

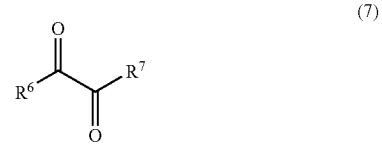

(7)

(wherein $R^6$ and $R^7$ are same with or different from each other and each represent a hydrocarbon group which may have a substituent); and the enamide compound is represented by the following formula (2):

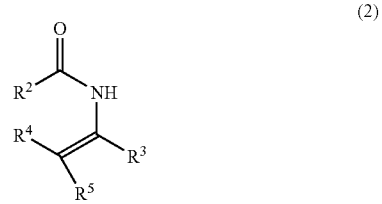

(2)

(wherein $R^2$ represents a hydrocarbon group which may have a substituent or a hydrocarbon group which may have a substituent to be bonded via an oxygen atom;

$R^3$ represents a hydrocarbon group which may have a substituent;

$R^4$ and $R^5$ may be same with or different from each other and each represent a hydrogen atom or a hydrocarbon group which may have a substituent, wherein at least one of them represents a hydrogen atom; and $R^3$ may form a ring by being bonded with $R^4$ or $R^5$).

According to a twelfth aspect of the invention, there is provided a method for synthesizing an optically active hydroxydiketone compound which is characterized in that, after this nucleophilic addition reaction, an acid treatment is performed, to thereby generate an optical active compound represented by the following formula (8):

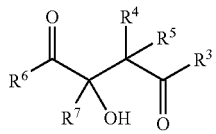

(8)

(wherein $R^6$, $R^7$, $R^3$, $R^4$ and $R^5$ each represent same article as described above).

BEST MODE FOR CARRYING OUT THE INVENTION

The present invention has characteristics as described above and is, further, described with reference to embodiments thereof.

In a method of an enantioselective nucleophilic addition reaction of enamide to a carbonyl group according to the invention, a chiral copper catalyst or a chiral nickel catalyst is used as a catalyst. As for the chiral catalyst on this occasion, various types of such chiral catalysts in each of which a copper (Cu) or nickel (Ni) atom is indispensable for a constitution thereof and to each of which a chiral organic molecular structure is attached are considered. Ordinarily, the chiral catalyst is constituted by a copper compound or nickel compound and a chiral organic compound and, more practically, from the standpoint of reaction yield and enantioselectivity, the chiral catalyst constituted by a copper compound or nickel compound and a chiral diamine ligand compound is favorably considered. The copper compound or nickel compound may be selected from among various types of salts, complex salts, organic metal compounds and the like as a monovalent or bivalent compound and, among other things, a salt with an organic or inorganic acid, a complex or organic composite of the salt is favorably mentioned. Among these compounds, a salt with a strong acid, for example, a salt of (per)fluoroalkyl sulfonic acid, perchloric acid or sulfonic acid, a complex or an organic composite of the salt is favorably illustrated. For example, $Cu(OTf)_2$, $CuClO_4$, $CuClO_4 \cdot 4CH_3CN$, $Cu(ClO_4)_2 \cdot 6H_2O$, $Ni(OTf)_2$, and $NiX_2+AgOTf$ (X being a halogen atom) are mentioned.

As for the chiral diamine ligand as a counterpart, an article having an ethylene diamine structure in a molecular constitution as a portion thereof is favorably used. On this occasion, an amino group may contain an imine bond. For example, as representatives, various types represented by the following formulae are illustrated:

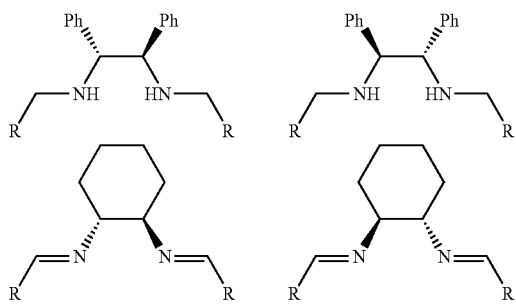

-continued

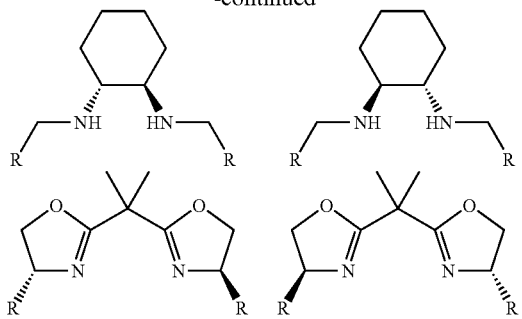

On this occasion, R in the formulae represents a hydrocarbon group which may have a substituent. The hydrocarbon group may be any one of various types in a chain state or a cyclic state and may have, as a substituent, a halogen atom, a hydrocarbon group of an alkyl group or the like, an alkoxy group or the like. Further, Ph (phenyl group) and a cyclohexyl group in the formulae may each have a substituent.

With reference to the chiral catalyst containing copper or nickel as described above according to the invention, a complex may previously be prepared by using a copper compound or a nickel compound and a chiral organic molecule and, then, used as a catalyst, or the copper compound or the nickel compound and the chiral organic molecule may be mixed with each other in a reaction system and, then, used. As far as a ratio in use as a catalyst is concerned, the copper compound or nickel compound or the complex of the copper compound or nickel compound and the chiral organic molecule is used at a rate of ordinarily from about 0.5 to about 30% by mol against the carbonyl compound.

The carbonyl compound to be used in the reaction may have any type of structure of an aliphatic, alicyclic, aromatic or a heterocyclic carbonyl compound or the like which may have a substituent, so long as it does not interfere with the nucleophilic addition reaction according to the present invention. For example, such carbonyl compound as described above may be the compound having the carbonyl group represented by the following formula as described above:

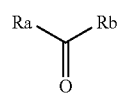

(wherein Ra represents a hydrocarbon group which may have a substituent, $R^0$—CO— or $R^0$—O—CO—, wherein $R^0$ represents a hydrocarbon group which may have a substituent; and Rb represents a hydrogen atom or a hydrocarbon group which may have a substituent).

For example, as for the compound having a carbonyl group, a glyoxylic acid ester represented by the formula (1) is illustrated. This article has an ester bond portion and reference mark $R^1$ in the formula represents a hydrocarbon group which may have a substituent. The hydrocarbon group may be any one of various types of hydrocarbon groups, for example, a chain or an alicyclic hydrocarbon group, an aromatic hydrocarbon group and mixtures thereof. As for such substituents, so long as they do not interfere with the nucleophilic addition reaction, the hydrocarbon group may appropriately have any one of various types of substituents such as a hydrocarbon group such as an alkyl group, an alkoxy group, a sulfide group, a cyano group, a nitro group, and an ester group.

The enamide compound as a counterpart can, for example, be represented by the above-described formula (2). As for characteristics thereof, it has an amide bond or a carbamate bond. As for reference marks in the formula, $R^2$ represents a hydrocarbon group which may have a substituent or a hydrocarbon group which may have a substituent to be bonded via an oxygen atom; $R^3$ represents a hydrocarbon group which may have a substituent; and $R^4$ and $R^5$ may be same with or different from each other and each represent a hydrogen atom or a hydrocarbon group which may have a substituent, in which at least one of them represents a hydrogen atom.

The hydrocarbon group may be any one of various types of hydrocarbon groups in a same manner as described above, for example, an aliphatic hydrocarbon group, an alicyclic hydrocarbon group, an aromatic hydrocarbon group and mixtures thereof. As for such substituents, various types of substituents such as a hydrocarbon group such as an alkyl group, a halogen atom, an alkoxy group, a sulfide group, a cyano group, a nitro group, and an ester group are appropriately be considered.

Further, as for reference mark $R^2$, a hydrocarbon group which is bonded via an oxygen atom such as —OEt, —O$^t$Bu, or —OBn is appropriately illustrated. As for reference mark $R^3$, an article having a substituent such as a phenyl group, a naphthyl group, or any one of these groups each having a substituent such as a halogen atom, an alkyl group, or an alkoxy group is favorably illustrated. In the nucleophilic addition reaction of the enamide compound to the aldehyde group (—CHO) of the glyoxylic acid ester, an appropriate organic solvent, for example, a halogenated hydrocarbon, any one of nitrites such as acetonitrile, or any one of ethers such as THF may be used and, in a reaction temperature, a range of from about −20° C. to about 40° C. can appropriately be adopted. A ratio of the aldehyde compound to the enamide compound to be used in an atmosphere of the air or in an inert atmosphere can appropriately be set to be in the range of from about 0.1 to about 10 in terms of a molar ratio.

In the nucleophilic addition reaction of the enamide compound, when a reaction between the glyoxylic acid ester represented by the above-described formula (1) and the enamide compound represented by the above-described formula (2) is taken as an example, an optically active α-hydroxy-γ-imino acid ester represented by at least one of the following formulae is enantioselectively generated:

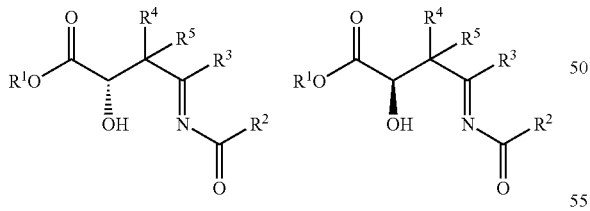

Then, particularly, when enecarbamate is used as a type of the enamide compound, a high stereoselectivity can also be realized. A syn-adduct and an anti-adduct can be obtained from a Z-body and an E-body at high diastereoselectivity and high enantioselectivity, respectively. By either without isolating or isolating the above-described imino acid ester compound, an acid treatment, for example, an acid treatment by using an aqueous solution of HCl, HBr or the like is performed, to thereby obtain the optically active α-hydroxy-γ-keto acid ester represented by the above-described formula (3) at high yield and with excellent enantioselectivity.

Further, on the other hand, without performing the acid treatment but performing a reduction treatment, the optically active α-hydroxy-γ-amino acid ester represented by the above-described formula (4) can be obtained at high yield and with excellent enantioselectivity in a same manner as described above. The reduction treatment on this occasion can use, for example, a boron reducing agent compound such as $Et_2BOMe$—$NaBH_4$, any one of other metal hydrides or a metallic hydrogen complex compound. Then, the thus-generated optically active α-hydroxy-γ-amino acid ester is subjected to a cyclization reaction to remove an acyl group on a γ-amino group therefrom (freeing from protection), to thereby being favorably converted into any one of optically active α-hydroxy-γ-lactams represented by the formula (5). For example, when the acyl group is a benzyloxycarbonyl group, protection freeing-cyclization reaction can be performed by catalytic hydrogen reduction.

Further, in the present invention, it is possible to synthesize the optically active α-hydroxy-γ-lactams as represented by the above-described formula (6) by subject the optically active α-hydroxy-γ-keto acid ester as described above firstly to a reduction reaction and, then, to a cyclization reaction.

Then, in the present invention, it is illustrated as a favorable example that a compound having a carbonyl group is a diketone compound as is represented by the above-described formula (7). Reference marks $R^6$ and $R^7$ in the formula (7) may be various types of hydrocarbon groups in a same manner as described above. It is possible to synthesize an optically active hydroxydiketone compound as shown in the formula (8) by performing the nucleophilic addition reaction of the enamide compound of the formula (2) on this diketone compound.

Hereinafter, the present invention is described in detail with reference to embodiments. It goes without saying that the present invention is not limited to these embodiments.

EXAMPLES

In Examples described below, unless stated otherwise, reference numerals and marks of chiral diamine ligands are denoted as follows:

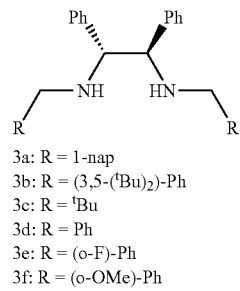

3a: R = 1-nap
3b: R = (3,5-($^t$Bu)$_2$)-Ph
3c: R = $^t$Bu
3d: R = Ph
3e: R = (o-F)-Ph
3f: R = (o-OMe)-Ph

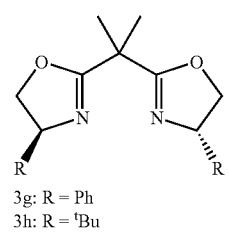

3g: R = Ph
3h: R = $^t$Bu

-continued

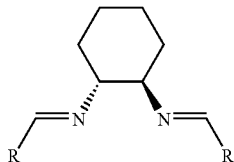

3i: R = Ph
3j: R = 1-nap
3k: R = 2-nap
3l: R = (3,5-di$^t$Bu)-C$_6$H$_3$
3m: R = o-Tol
3n: R = m-Tol
3o: R = p-Tol
3p: R = p-Et-C$_6$H$_4$
3q: R = p-$^i$Pr-C$_6$H$_4$
3r: R = p-F-C$_6$H$_4$
3s: R = p-Cl-C$_6$H$_4$
3t: R = p-Br-C$_6$H$_4$

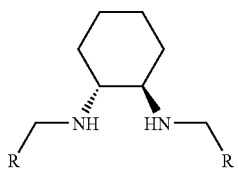

3v: R = Ph
3w: R = 2-nap
3x: R = (3,5-($^t$Bu)$_2$)-Ph

Example 1

In the formula described below, a CH$_2$Cl$_2$ (1.5 ml) solution of chiral diamine ligand (9.9 mg, 0.022 mmol) in which R represents 4-BrC$_6$H$_4$ is added to CuClO$_4$·4CH$_3$CN (6.5 mg, 0.020 mmol) in an argon atmosphere and the resultant excellent yellow solution was stirred for 8 hours or more and, then, cooled to 0° C.

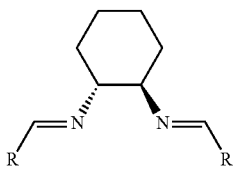

Next, into the resultant mixed solution, a CH$_2$Cl$_2$ (0.8 ml) solution of ethyl glyoxylate (100 μl, 0.40 mmol) represented by the formula described below was added and, further, a CH$_2$Cl$_2$ (0.8 ml) solution of enamide (0.20 mmol) represented by the formula (2) as shown in Table 1 was added.

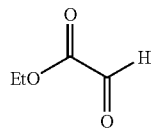

The resultant reaction mixed solution was stirred for one hour at 0° C. and, then, added with a saturated aqueous solution of NaHCO$_3$, to thereby terminate a reaction. Thereafter, the resultant reaction mixed solution was allowed to have room temperature and, then, subjected to extraction by using CH$_2$Cl$_2$. The resultant organic phase was rinsed and, then, dried. After a solvent was evaporated, a residue was dissolved in EtOH (3.0 ml), added with a 48% aqueous HBr solution (0.3 ml) and, then, stirred for 1.5 minute at room temperature.

The resultant reaction mixture was subjected to extraction by using CH$_2$Cl$_2$. The resultant organic phase was rinsed and, then, dried. After a solvent was evaporated, a crude product was obtained. This crude product was purified by using silica gel chromatography.

In Table 1, the reaction yield and ee (%) in accordance with the type of enamide are shown. On this occasion, the ee (%) was determined by an HPLC analysis.

TABLE 1

| No. | R$^2$ | R$^3$ | R$^4$, R$^5$ | Yield (%) | ee (%) |
|---|---|---|---|---|---|
| 1-1 | BnO | Ph | H, H | 93 | 97 |
| 1-2 | BnO | 4-MeO—Ph | H, H | 94 | 93 |
| 1-3 | BnO | 4-Cl—Ph | H, H | 97 | 97 |
| 1-4 | BnO | 4-Me—Ph | H, H | quantum | 96 |
| 1-5 | BnO | 2-naphthyl | H, H | 91 | 96 |

Identification values of products in the case of Nos. 1-1 to 1-5 are shown below.

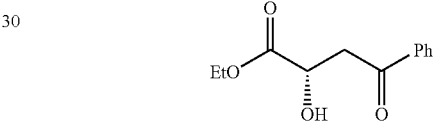

(2S)-2-Hydroxy-4-oxo-4-phenyl-butyric acid ethyl ester: $^1$H NMR (CDCl$_3$) δ=1.27 (t, 3H, J=7.1 Hz), 3.29 (brs, 1H), 3.44 (dd, 1H, J=6.1, 17.6 Hz), 3.52 (dd, 1H, J=3.9, 17.6 Hz), 4.25 (q, 2H, J=7.1 Hz), 4.61-4.67 (m, 1H), 7.44-7.50 (m, 2H), 7.54-7.60 (m, 1H), 7.92-7.98 (m, 2H); $^{13}$C NMR (CDCl$_3$) δ=14.0, 42.1, 61.8, 67.1, 128.1, 128.6, 133.5, 136.4, 173.7, 197.5. IR (neat) 3475, 3063, 2983, 1737, 1687, 1597, 1580, 1449, 1368, 1213, 1098, 1045, 860, 759, 690, 582, 499 cm$^{-1}$; HRMS (FAB); Exact mass calcd for C$_{12}$H$_{15}$O$_4$ [M+H]$^+$, 223.0970. Found 223.0972; HPLC, Daicel Chiralcel ADH, hexane/$^i$PrOH=4/1, flow rate=0.5 mL/min: t$_R$=19.9 min (S), t$_R$=22.2 min (R).

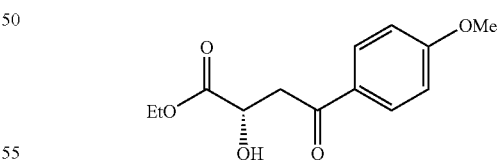

(2S)-2-Hydroxy-4-(4-methoxy-phenyl)-4-oxo-butyric acid ethyl ester: $^1$H NMR (CDCl$_3$) δ=1.28 (t, 3H, J=7.1 Hz), 3.41 (dd, 1H, J=5.9, 17.4 Hz), 3.48 (dd, 1H, J=4.0, 17,4 Hz), 3.48 (brd, 1H, J=6.8 Hz), 3.87 (s, 3H), 4.26 (q, 2H, J=7.1 Hz), 4.60-4.70 (m, 1H), 6.91-6.97 (m, 2H), 7.90-7.97 (m, 2H); $^{13}$C NMR (CDCl$_3$) δ=14.0, 41.7, 55.4, 61.7, 67.3, 113.8, 129.5, 130.4, 163.8, 173.8, 196.1. IR (neat) 3483, 2979, 2841, 1739, 1677, 1600, 1575, 1512, 1465, 1421, 1368, 1265, 1172, 1099, 1027, 988, 895, 834, 737, 579 cm$^{-1}$; HRMS (FAB); Exact mass calcd for C$_{13}$H$_{17}$O$_5$ [M+H]$^+$, 253.1076. Found 253.1097.; HPLC, Daicel Chiralcel ADH, hexane/$^i$PrOH=4/1, flow rate=0.4 mL/min: $t_R$=43.1 min (S), $t_R$=45.7 min (R).

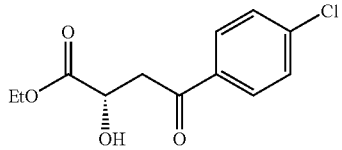

(2S)-4-(4-Chloro-phenyl)-2-hydroxy-4-oxo-butyric acid ethyl ester; $^1$H NMR (CDCl$_3$) δ=1.28 (t, 3H, J=7.1 Hz), 3.42 (dd, 1H, J=6.1, 17.3 Hz), 3.49 (dd, 1H, J=3.9, 17.3 Hz), 3.41-3.47 (brd, 1H), 4.26 (q, 2H, J=7.1 Hz), 4.62-4.70 (m, 1H), 7.42-7.48 (m, 2H), 7.86-7.93 (m, 2H); $^{13}$C NMR (CDCl$_3$) δ=14.1, 42.2, 62.0, 67.1, 129.0, 129.6, 134.8, 140.1, 173.7, 196.3. IR (neat) 3480, 2982, 1739, 1684, 1590, 1573, 1402, 1213, 1093, 1045, 820, 531 cm$^{-1}$; HRMS (FAB); Exact mass calcd for C$_{12}$H$_{14}$ClO$_4$ [M+H]$^+$. 257.0580. Found 257.0584.; HPLC, Daicel Chiralcel ADH, hexane/$^i$PrOH=4/1, flow rate=0.5 mL/min: $t_R$=24.2 min (S), $t_R$=26.5 min (R).

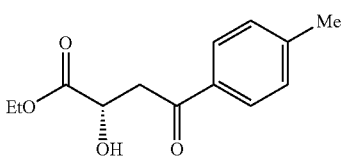

(2S)-2-Hydroxy-4-oxo-4-p-tolyl-butyric acid ethyl ester; $^1$H NMR (CDCl$_3$) δ=1.28 (t, 3H, J=7.1 Hz), 2.41 (s, 3H), 3.44 (dd, 1H, J=5.9, 17.4 Hz), 3.51 (dd, 1H, J=4.0, 17.4 Hz), 3.45-3.55 (brs, 1H), 4.26 (q, 2H, J=7.1 Hz), 4.66 (dt, 1H, J=4.2, 5.5 Hz), 7.26 (apparent d, 2H, J=8.0 Hz), 7.85 (apparent d, 2H, J=8.2 Hz); $^{13}$C NMR (CDCl$_3$) δ=14.0, 21.6, 42.0, 61.7, 67.2, 128.2, 129.3, 133.9, 144.4, 173.7, 197.1. IR (neat) 3483, 2981, 1742, 1682, 1606, 1405, 1365, 1212, 1098, 1044, 813, 578 cm$^{-1}$; HRMS (FAB); Exact mass calcd for C$_{13}$H$_{17}$O$_4$ [M+H]$^+$, 237.1127. Found 237.1120.; HPLC, Daicel Chiralcel ADH, hexane/$^i$PrOH=4/1, flow rate=0.3 mL/min: $t_R$=36.1 min (S), $t_R$=38.2 min (R).

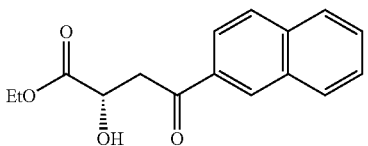

(2S)-2-Hydroxy-4-naphthalen-2-yl-4-oxo-butyric acid ethyl ester; $^1$H NMR (CDCl$_3$) δ=1.28 (t, 3H, J=7.1 Hz), 3.52 (d, 1H, J=5.9 Hz), 3.59 (dd, 1H, J=6.1, 17.3 Hz), 3.66 (dd, 1H, J=3.9, 17.3 Hz), 4.28 (q, 2H, J=7.1 Hz), 4.73 (dt, 1H, J=4.2, 5.4 Hz), 7.50-7.65 (m, 2H), 7.82-8.20 (m, 4H), 8.45 (s, 1H); $^{13}$C NMR (CDCl$_3$) δ=14.1, 42.3, 61.9, 67.3, 123.6, 126.9, 127.8, 128.6, 128.8, 129.6, 130.2, 132.4, 133.8, 135.8, 173.9, 197.5. IR (neat) 3481, 3058, 2982, 1741, 1681, 1627, 1469, 1369, 1209, 1097, 1045, 859, 824, 749, 477 cm$^{-1}$; HRMS (FAB); Exact mass calcd for C$_{16}$H$_{17}$O$_4$ [M+H]$^+$, 273.1127. Found 273.1125.; HPLC, Daicel Chiralcel ADH, hexane/$^i$PrOH=4/1, flow rate=0.5 mL/min: $t_R$=27.0 min (S), $t_R$=30.4 min (R).

Example 2

An nucleophilic addition reaction of enamide was performed by various types of chiral diamine ligands and CuClO$_4$-4CH$_3$CN, while using No. 1-1 enamide and ethyl glyoxylate in Example 1 and, to thereby synthesize an α-hydroxy-γ-imino acid ester.

The results are shown in Table 2.

TABLE 2

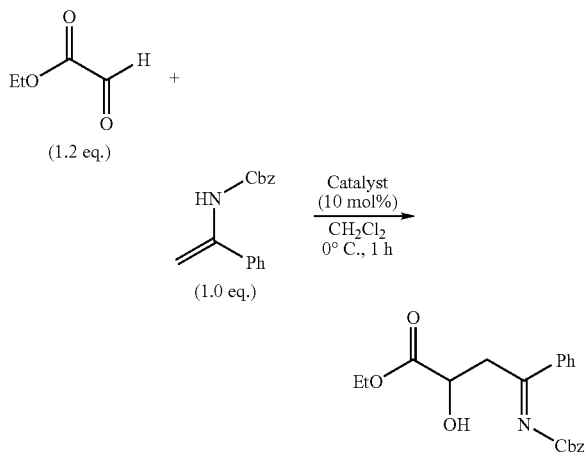

| entry | metal | ligand | yield (%) | ee (%)$^a$ |
|---|---|---|---|---|
| 1 | CuClO$_4$•4CH$_3$CN | 3a | 90 | 35$^a$ |
| 2 | CuClO$_4$•4CH$_3$CN | 3i | 94 | 93 |
| 3 | CuPF$_6$•4CH$_3$CN | 3i | 94 | 82 |
| 4 | CuOTf•0.5C$_6$H$_5$CH$_3$ | 3i | 66 | 78 |
| 5 | CuClO$_4$•4CH$_3$CN | 3j | 92 | 73 |
| 6 | CuClO$_4$•4CH$_3$CN | 3k | 52 | 68 |
| 7$^b$ | CuClO$_4$•4CH$_3$CN | 3i | 48 | 91 |
| 8$^c$ | CuClO$_4$•4CH$_3$CN | 3i | 97 | 93 |
| 9$^d$ | CuClO$_4$•4CH$_3$CN | 3i | quant | 94 |
| 10$^d$ | CuClO$_4$•4CH$_3$CN | 3m | 97 | 81 |
| 11$^d$ | CuClO$_4$•4CH$_3$CN | 3n | quant | 86 |
| 12$^d$ | CuClO$_4$•4CH$_3$CN | 3o | 98 | 95 |
| 13$^d$ | CuClO$_4$•4CH$_3$CN | 3p | 87 | 94 |
| 14$^d$ | CuClO$_4$•4CH$_3$CN | 3q | 93 | 94 |
| 15$^d$ | CuClO$_4$•4CH$_3$CN | 3r | 97 | 96 |
| 16$^d$ | CuClO$_4$•4CH$_3$CN | 3s | 93 | 96.5 |
| 17$^d$ | CuClO$_4$•4CH$_3$CN | 3t | 93 | 97.0 |

$^a$The absolute configuration is S except in entry 1 (R).
$^b$−78° C.
$^c$Ethyl glyoxylate (1.5 equiv) was used.
$^d$Ethyl glyoxylate (2.0 equiv) was used.

Example 3

A reaction was performed in a same manner as in Example 2 except that various types of enamides were used and an amount of CuClO$_4$-4CH$_3$CN to be used was changed. The results are shown in Table 3. It is found that results of high yield and high ee % can be obtained even with a low concentration of a chiral copper catalyst.

TABLE 3

13

[Scheme: 2 (HN-Cbz, vinyl, R) + CuClO₄·4CH₃CN, 3t (x mol%), CH₂Cl₂, 0 °C, 1 h → EtO-C(=O)-CH(OH)-CH₂-C(=N-Cbz)-R]

| entry | 2 | x (mol %) | yield (%) | ee (%) |
|---|---|---|---|---|
| 1 | 2a (R = Ph) | 10 | 93 | 97 |
| 2 | 2a | 5 | 94 | 96 |
| 3 | 2a | 2 | 96 | 95 |
| 4 | 2a | 1 | 90 | 94 |
| 5 | 2b (R = PMP) | 10 | 94 | 93 |
| 6 | 2c (R = PCP) | 10 | 97 | 97 |
| 7 | 2d (R = PMeP) | 10 | quant | 96 |
| 8 | 2e (R = 2-Nap) | 10 | 91 | 96 |

Cbz = Benzyloxycarbonyl.
PMP = p-Methoxyphenyl.
PCP = p-Chlorophenyl.
PMeP = p-Methylphenyl.
2-Nap = 2-Naphthyl.

Example 4

A reaction was performed in a same manner as in Example 2 except that Cu(OTf)₂ or the like was used in place of the copper compound.

The results are shown in Table 4. An absolute configuration of the product was R.

TABLE 4

[Scheme: EtO-C(=O)-C(=O)H  5 (1.2 eq.) + HN(Cbz)-C(=CH₂)-R  2a (1.0 eq.) → Catalyst (10 mol%), CH₂Cl₂, 0 °C, 1 h → EtO-C(=O)-CH(OH)-CH₂-C(=N-Cbz)-Ph  6a]

| entry | metal | ligand | yield (%) | ee (%)ᵈ |
|---|---|---|---|---|
| 1 | Cu(OTf)₂ | 3a | 93 | 55 |
| 2ᵃ | Cu(OTf)₂ | 3a | 91 | 54 |
| 3ᵇ | Cu(OTf)₂ | 3a | 89 | 58 |
| 4 | Cu(OTf)₂ | 3b | 74 | 59 |
| 5 | Cu(OTf)₂ | 3c | 58 | 57 |
| 6 | Cu(OTf)₂ | 3d | 98 | 46 |
| 7 | Cu(OTf)₂ | 3e | 97 | 37 |
| 8 | Cu(OTf)₂ | 3h | 70 | 73 |
| 9 | Cu(OTf)₂ | 3i | 65 | 70 |
| 10 | Cu(OTf)₂ | 3j | 66 | 28 |
| 11 | Cu(OTf)₂ | 3k | 71 | 52 |
| 12 | Cu(OTf)₂ | 3l | 68 | 17 |
| 13 | Cu(OTf)₂ | 3v | 89 | 51 |
| 14 | Cu(OTf)₂ | 3w | 91 | 50 |
| 15 | Cu(OTf)₂ | 3x | quant | 62 |
| 16 | Cu(SbF₆)₂ | 3b | 77 | 44 |

ᵃCatalyst (30 mol %) was used.
ᵇ−20 °C.

Example 5

A treatment as described below was performed in place of the acid treatment by using the aqueous HBr solution in Example 1-1.

Namely, the residue was added with a mixed solution of THF (2.0 ml) and MeOH (0.5 ml) and, then, cooled to −78° C. and, thereafter, added with Et₂BOMe (79 μl, 0.6 mmol) and, subsequently, stirred for 15 minutes. The resultant mixed solution was added with NaBH₄ (22.7 mg, 0.6 mmol) and, then, cooled to −78° C. and stirred for 2 hours at this temperature.

Then, a reaction was terminated by being added with AcOH (0.3 μl) and, then, allowed to have room temperature.

The compound described below was obtained in an amount of 46.5 mg at a yield of 65%. A ratio of syn/anti was 94/6.

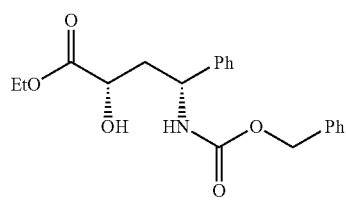

4-Benzyloxycarbonylamino-2-hydroxy-4-phenyl-butyric acid ethyl ester: (10, syn/anti=94/6): ¹H NMR (CDCl₃) δ=1.23 (t, 3H×19/20, J=7.1 Hz), 1.25 (t, 3H ×1/20, J=7.0 Hz), 1.95-2.40 (m, 2H), 3.33 (brs, 1H×19/20), 3.51 (brs, 1H×1/20). 4.00-4.40 (m, 3H), 4.85-5.20 (m, 3H), 5.52 (d, 1H×19/20, J=7.3 Hz), 5.96 (d, 1H×1/20, J=8.2 Hz), 7.00-7.60 (m, 10H); ¹³C NMR (CDCl₃) syn: δ=14.1, 40.3, 52.6, 61.8, 66.8, 68.4, 126.4, 127.6, 128.1, 128.4, 128.7, 136.3, 141.4, 155.7, 174.4; anti: (distinguishable peak) 40.2, 52.4, 67.8, 126.2, 127.4, 141.1, 156.0, 174.3; LRMS (FAB) m/z=358 (M+H⁺)

In the same manner as described above, when a reaction was performed for 3 hours in the solvent of $Et_2O$ by using $Zn(BH_4)_2$ (one equivalent), the results in which the yield was 66% and a ratio of syn/anti was 78/22 were obtained.

Example 6

In accordance with the following reaction formulae, γ-lactams (12) were synthesized from the product obtained in Example 5:

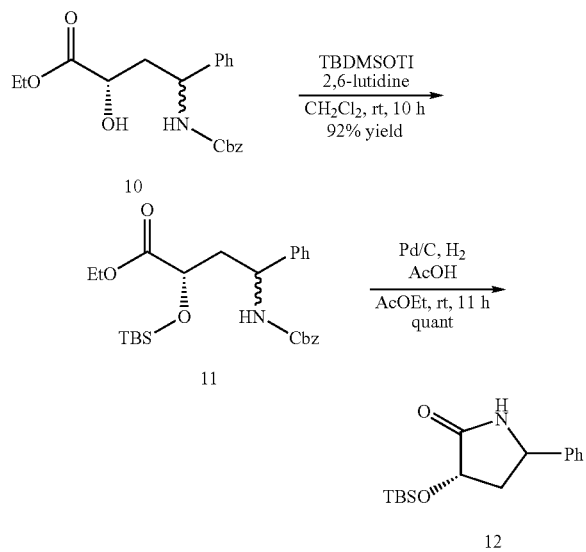

1) A $CH_2Cl_2$ (0.6 ml) solution of the above-described product (10) (31.3 mg, 0.08 mmol) was added with a $CH_2Cl_2$ (0.2 ml) solution of 2.6-lutidine (12.0 mg, 0.114 mmol) and a $CH_2Cl_2$ solution of tert-butyl dimethyl silyl trifluoromethane sulfonate: TBDMSOTf (27.8 mg, 0.105 mmol) at a temperature of 0° C.

A reaction mixture was stirred for 10 hours at room temperature.

After the resultant reaction mixture was added with water, it was subjected to extraction by, using $CH_2Cl_2$ and, then, the resultant organic phase was rinsed and, then, dried and, thereafter, a solvent therein was evaporated. The resultant crude product was purified by using silica gel chromatography, to thereby obtain 37.9 mg (with a yield of 92%) of a next compound (11).

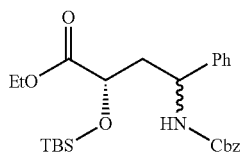

4-Benzyloxycarbonylamino-2-(tert-butyl-dimethyl-silanyloxy)-4-phenyl-butyric acid ethyl ester (11, diastereomer mixture): ¹H NMR (CDCl₃) δ=syn: −0.03 (s, 3H), 0.02 (s, 3H), 0.90 (s, 9H), 1.15-1.27 (m, 3H), 2.00-2.35 (m, 2H), 3.90-4.30 (m, 3H), 4.80-5.15 (m, 3H), 5.50 (brs, 1H), 7.15-7.40 (m, 10H); anti: (distinguishable peak) δ=−0.02 (s, 3H), 0.03 (s, 3H), 5.62 (brd, 1H, J=7.7 Hz); ¹³C NMR (CDCl₃) syn: δ=−5.4, −5.0, 14.0, 18.1, 25.7, 41.0, 52.9, 61.0, 66.6, 70.3, 126.4, 127.4, 128.0, 128.1, 128.4, 128.6, 136.4, 141.8, 155.3, 173.2; anti: (distinguishable peak) −5.0. 14.1, 41.8, 52.3, 69.8, 126.0, 127.3, 128.6, 142.2, 155.6, 173.1; IR (neat) 3343, 2940, 1720, 1518, 1254, 1131, 1038, 839, 781, 699 cm⁻¹; HRMS (FAB); Exact mass calcd for $C_{26}H_{38}NO_5Si$ [M+H]⁺, 472.2519. Found 472.2508.

2) An AcOEt (2.0 ml) solution of the above-described product (11) (21.4 mg, 0.454 mmol) was added with AcOH (16.8 mg, 0.0272 mmol) and a 5% Pd/C (9.7 mg, 10% by mol) at room temperature. After an argon gas in the atmosphere of the resultant mixture was replaced with an $H_2$ gas, the mixture was stirred for 11 hours, to thereby obtain a next compound (12) (13.4 mg, quantitative yield). A diastereomer (12) can be separated by using silica gel chromatography.

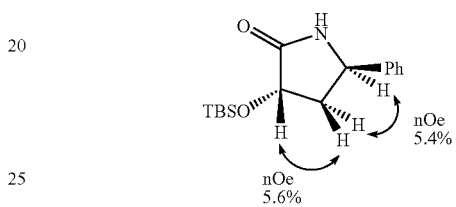

(3S, 5R)-3-(tert-Butyl-dimethyl-silanyloxy)-5-phenyl-pyrrolidin-2-one (12-major): ¹H NMR (CDCl₃) δ=0.14 (s, 3H), 0.16 (s, 3H), 0.91 (s, 9H), 2.21 (ddd, 1H, J=5.1, 7.1, 13.2 Hz), 2.46 (ddd, 1H, J=5.1, 7.5, 13.2 Hz), 4.38 (dd, 1H, J=5.1, 7.1 Hz), 4.83 (dd, 1H, J=5.0, 7.5 Hz), 6.02 (brs, 1H), 7.20-7.43 (m, 5H); ¹³C NMR (CDCl₃) δ=−5.1, −4.5, 18.3, 25.8, 41.5, 55.1, 69.9, 125.5, 127.9, 129.0, 142.1, 176.3; IR (neat) 3226, 2927, 2892, 2855, 1715, 1496, 1471, 1331, 1253, 1151, 1091, 1028, 963, 880, 839, 780, 699 cm⁻¹; HRMS (FAB); Exact mass calcd for $C_{16}H_{26}NO_2Si$ [M+H]⁺, 292.1733. Found 292.1733.;

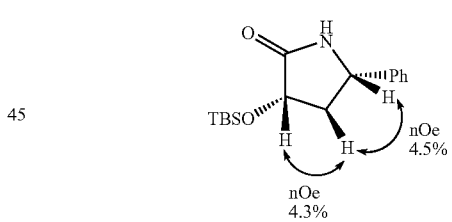

(3S, 5S)-3-(tert-Butyl-dimethyl-silanyloxy)-5-phenyl-pyrrolidin-2-one (12-minor): ¹H NMR (CDCl₃) δ=0.15 (s, 3H), 0.20 (s, 3H), 0.91 (s, 9H), 1.94 (dt, 1H, J=9.2, 12.6 Hz), 2.75-2.87 (m, 1H), 4.42 (dd, 1H, J=7.9, 9.2 Hz), 4.53 (dd, 1H, J=6.2, 8.6 Hz), 5.76 (brs, 1H), 7.30-7.40 (m, 5H); ¹³C NMR (CDCl₃) δ=−5.1, −4.5, 118.3, 25.8, 42.0, 53.9, 70.8, 126.1, 128.2, 128.9, 176.0; IR (neat) 3220, 2936, 2858, 2359, 1717, 1463, 1330, 1247, 1151, 882, 838, 781, 698 cm⁻¹; HRMS (FAB); Exact mass calcd for $C_{16}H_{26}NO_2Si$ [M+H]⁺, 292.1733. Found 292.1736.;

Example 7

A reaction was performed in a same manner as in Example 1 except that various types of enecarbamates shown in Table 10 as enamides represented by the above-described formula (2) were used. In Table 5, yield (%), a syn/anti ratio, and ee (%) of a reaction product are shown. Identification values of 7-1/7-2, 7-3/7-4, 7-5/7-6 and 7-7/7-8 of the reaction products are also shown.

From the results of this reaction, it was confirmed that an anti-adduct and a syn-adduct were obtained from an E-body and a Z-body at high diastereoselectivity and high enantioselectivity, respectively.

TABLE 5

| No. | $R^2$ | $R^3$ | $R^4, R^5$ | Yield (%) | Syn/anti | ee (%) |
|---|---|---|---|---|---|---|
| 7-1 | BnO | Ph | Me, H (E) | 83 | 1/99 | 98 |
| 7-2 | BnO | Ph | H, Me (Z) | 82 | 98/2 | 98 |
| 7-3 | BnO | 4-MeO—Ph | Me, H (E) | 96 | 2/98 | 98 |
| 7-4 | BnO | 4-MeO—Ph | H, Me (Z) | 97 | 98/2 | 98 |
| 7-5 | EtO | 4-MeO—Ph | Me, H (E) | 82 | 3/97 | 96 |
| 7-6 | EtO | 4-MeO—Ph | H, Me (Z) | 96 | 99/1 | 98 |
| 7-7 | BnO | 4-Cl—$C_6H_4$ | Me, H (E) | 85 | 2/98 | 98 |
| 7-8 | BnO | 4-Cl—$C_6H_4$ | H, Me (Z) | 79 | 99/1 | 98 |

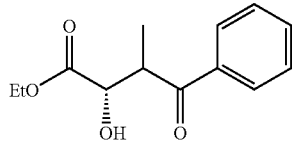

(2S)-2-Hydroxy-3-methyl-4-oxo-4-phenyl-butyric acid ethyl ester (syn/anti mixture): $^1$H NMR syn (CDCl$_3$) δ=1.26 (t, 3H, J=7.0 Hz), 1.29 (d, 3H, J=7.0 Hz), 3.28 (br, (1H), 3.93 (dq, 1H, J=4.2, 7.0 Hz), 4.25 (q, 2H, J=7.0 Hz), 4.58 (d, 1H, J=4.2 Hz), 7.40-7.65 (m, 3H), 7.90-8.05 (m, 2H); anti (CDCl$_3$) δ=1.20 (t, 3H, J=7.1 Hz), 1.36 (d, 3H, J=7.3 Hz), 3.61 (d, 1H, J=8.3 Hz), 3.98 (dq, 1H, J=4.6, 7.1 Hz), 4.10-4.25 (m, 2H), 4.39 (dd, 1H, J=4.6, 8.3 Hz), 7.40-7.65 (m, 3H); $^{13}$C NMR syn (CDCl$_3$) δ=12.1, 14.0, 44.3, 61.9, 71.6, 128.4, 128.7, 133.3, 135.7, 173.1, 201.6; anti (CDCl$_3$) δ=14.0, 14.1, 44.0, 61.5, 73.1, 128.3, 128.7, 133.4, 135.9, 173.1; IR (neat) syn 3480, 3063, 2978, 2936, 1734, 1678, 1596, 1579, 1449, 1369, 1217, 1133, 1062, 1023, 1001, 975, 952, 862, 794, 708; anti 3481, 3059, 2981, 2941, 1738, 1685, 1588, 1454, 1372, 1255, 1209, 1144, 1092, 1024, 973, 701 cm$^{-1}$; HRMS (FAB); Exact mass calcd for $C_{13}H_{17}O_4$ [M+H]$^+$, 237.1118.; HPLC, Daicel Chiralcel AS+ADH+AD, hexane/$^i$PrOH=4/1, flow rate=0.5 mL/min: $t_R$=46.7 min (2S, 3S), $t_R$=50.6 min (2R, 3R), $t_R$=54.3 min (2S, 3R), $t_R$=61.9 min (2R, 3S).

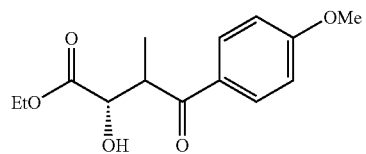

(2S)-2-Hydroxy-4-(4-methoxy-phenyl)-3-methyl-4-oxo-butyric acid ethyl ester (syn/anti mixture): $^1$H NMR syn (CDCl$_3$) δ=1.28 (t, 3H, J=7.1 Hz), 1.29 (d, 3H, J=7.1 Hz), 3.35 (br, 1H), 3.84-3.96 (m, 4H), 4.27 (q, 2H, J=7.1 Hz), 4.58 (t, 1H, J=4.2 Hz), 6.96 (apparent d, 2H, J=9.0 Hz), 7.30-7.45 (m, 5H) 7.95 (apparent d, 2H, J=8.8 Hz); anti (CDCl$_3$) δ=1.19 (t, 3H, J=7.1 Hz), 1.36 (d, 3H, J=7.3 Hz), 3.75 (d, 1H, J=9.3 Hz), 3.88 (s, 3H), 3.94 (dq, 1H, J=4.6, 7.3 Hz), 4.15 (apparent dq, 2H, J=3.2, 7.1 Hz), 4.36 (dd, 1H, J=4.6, 9.3 Hz), 6.92-6.99 (m, 2H), 7.90-7.97 (m, 2H); $^{13}$C NMR syn (CDCl$_3$) δ=12.3, 14.0, 43.7, 55.4, 61.8, 71.7, 113.9, 128.5, 130.7, 163.7, 173.1, 200.4; anti (CDCl$_3$) δ=14.0, 14.6, 43.2, 55.5, 61.4, 73.4, 113.9, 128.7, 130.8, 163.8, 173.2, 201.9; IR (neat) syn 3477, 2979, 2935, 2850, 1730, 1670, 1600, 1573, 1510, 1463, 1420, 1308, 1261, 1173, 1125, 1027, 976, 843, 770, 604; anti 3478, 2979, 2941, 2843, 1738, 1671, 1599, 1580, 1510, 1457, 1419, 1370, 1308, 1257, 1216, 1172, 1092, 1026, 974, 841 cm$^{-1}$; HRMS (FAB); Exact mass calcd for $C_{14}H_{19}O_5$ [M+H]$^+$, 267.1232, Found 267.1232.; HPLC, Daicel Chiralcel ADH, hexane/$^i$PrOH=4/1, flow rate=0.2 mL/min: $t_R$=60.5 min (2R, 3R), $t_R$=65.4 min (2S, 2S), $t_R$=75.2 min (2R, 3S), $t_R$=78.9 min (2S, 3R).

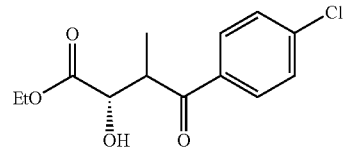

(2S)-4-(4-Chloro-phenyl)-2-hydroxy-3-mentyl-4-oxo-butyric acid ethyl ester (syn/anti mixture): $^1$H NMR syn (CDCl$_3$) δ=1.26 (t, 3H, J=7.0 Hz), 1.28 (d, 3H, J=7.0 Hz), 3.27 (brs, 1H), 3.87 (dq, 1H, J=4.4, 7.0 Hz), 4.25 (q, 2H, J=7.0 Hz), 4.55 (d, 1H, J=4.4 Hz), 7.40-7.55 (m, 2H), 7.84-7.97 (m, 2H); anti (CDCl$_3$) δ=1.21 (t, 3H, J=7.1 Hz), 1.34 (d, 3H, J=7.1 Hz), 3.53 (d, 1H, J=8.2 Hz), 3.91 (dq, 1H, J=5.0, 7.1 Hz), 4.08-4.24 (m, 2H), 4.38 (dd, 1H, J=5.0, 8.2 Hz), 7.42-7.52 (m, 2H), 7.80-7.95 (m, 2H); $^{13}$C NMR syn (CDCl$_3$) δ=12.1, 14.0, 44.4, 62.0, 71.5, 129.0, 129.8, 134.1, 139.7, 173.1, 200.3; anti (CDCl$_3$) δ=13.9, 14.0, 44.1, 61.6, 73.0, 129.0, 129.8, 134.3, 139.9, 173.0, 201.8; IR (neat) syn 3485, 2982, 2938, 1730, 1682, 1589, 1571, 1488, 1455, 1401, 1217, 1132, 1092, 1013, 977, 843, 758, 692, 533, 478; anti 3478, 3092, 2982, 2935, 1738, 1686, 1589, 1455, 1402, 1255, 1208, 1144, 1092, 1022, 976, 842, 751, 527 cm$^{-1}$; HRMS (FAB); Exact mass calcd for $C_{13}H_{16}ClO_4$ [M+H]$^+$, 271.0737. Found 271.0745.; HPLC, Daicel Chiralcel AS, hexane/$^i$PrOH=4/1, flow rate=0.5 mL/min: $t_R$=15.1 min (2S, 3S), $t_R$=16.6 min (2S, 3R), $t_R$=21.4 min (2R, 3S), $t_R$=23.9 min (2R, 3R).

Example 8

A reaction was performed in a same manner as in Example 7 except that various types of enecarbamates as shown in Table 6 were used. In Table 6, yield (%), a syn/anti ratio, and ee (%) of a reaction product are shown. Identification values of 8-1/8-2 and 8-3/8-4 of the reaction products are also shown.

It was confirmed that, in a same manner as in Example 7, an anti-adduct and a syn-adduct were obtained from an E-body and a Z-body at high diastereoselectivity and high enantioselectivity, respectively.

TABLE 6

| No. | R² | R³ | R⁴, R⁵ | Yield (%) | Syn/anti | ee (%) |
|---|---|---|---|---|---|---|
| 8-1 | BnO | Ph | Et, H (E) | 90 | 1/99 | 98 |
| 8-2 | BnO | Ph | H, Et (Z) | 92 | 99/1 | 98 |
| 8-3 | BnO | Et | Me, H (E) | 83 | 3/97 | 97 |
| 8-4 | BnO | Et | H, Me (Z) | 89 | 92/8 | 98 |

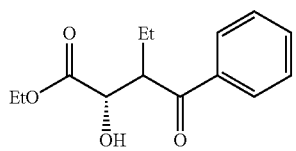

(2S)-3-Benzoyl-2-hydroxy-pentanoic acid ethyl ester (syn/anti mixture); $^1$H NMR syn (CDCl$_3$) δ=0.93 (t, 3H, J=7.5 Hz), 1.19 (t, 3H, J=7.1 Hz), 1.70-2.05 (m, 2H), 3.18 (brs, 1H), 3.83 (dt, 1H, J=5.3, 8.3 Hz), 4.19 (q, 2H, J=7.1 Hz), 4.51 (d, 1H, J=5.3 Hz), 7.42-7.54 (m, 2H), 7.54-7.62 (m, 1H), 7.90-8.02 (m, 2H); anti (CDCl$_3$) δ=1.04 (t, 3H, J=7.6 Hz), 1.15 (t, 3H, J=7.1 Hz), 1.80-1.95 (m, 2H), 3.70 (d, 1H, J=9.5 Hz), 3.83 (dt, 1H, J=4.2, 7.1 Hz), 4.09 (q, 2H, J=7.1 Hz), 4.43 (dd, 1H, J=4.2, 9.5 Hz), 7.46-7.52 (m, 2H), 7.56-7.63 (m, 1H), 7.88-7.95 (m, 2H); $^{13}$C NMR syn (CDCl$_3$) δ=12.0, 13.9, 21.3, 51.2, 61.9, 71.1, 128.3, 128.6, 133.2, 137.0, 173.6, 201.5; anti (CDCl$_3$) δ=12.0, 13.9, 22.3, 50.1, 61.4, 71.3, 128.3, 128.7, 133.5, 136.6, 173.4, 203.9; IR (neat) syn 3477, 2972, 2876, 1738, 1675, 1596, 1447, 1372, 1255, 1220, 1118, 1023, 931, 849, 779, 701; anti 3485, 3062, 2966, 2941, 2875, 1738, 1682, 1596, 1579, 1448, 1368, 1268, 1208, 1134, 1100, 1028, 914, 849, 785, 699 cm$^{-1}$; HRMS (FAB); Exact mass calcd for C$_{14}$H$_{19}$O$_4$ [M+H]$^+$, 251.1283. Found 251.1277.; HPLC, Daicel Chiralcel AS, hexane/$^i$PrOH=4/1, flow rate=0.5 mL/min: t$_R$=13.7 min (2S, 3S), t$_R$=15.3 min (2S, 3R), t$_R$=17.6 min (2R, 3R), t$_R$=23.1 min (2R, 3S).

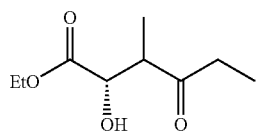

(2S)-2-Hydroxy-3-methyl-4-oxo-hexanoic acid ethyl ester (syn/anti mixture): $^1$H NMR syn (C$_6$D$_6$) δ=0.89 (t, 3H, J=7.1 Hz), 0.99 (d, 3H, J=7.2 Hz), 1.97-2.08 (m, 2H), 2.70 (dq, 1H, J =4.9, 7.2 Hz), 3.39 (d, 1H, J=6.7 Hz), 3.80-4.00 (m, 2H), 4.11 (dd, 1H, J=4.9, 6.7 Hz); anti (C$_6$D$_6$) δ=0.87 (t, 3H, J=7.1 Hz), 0.93 (t, 3H, J=7.3 Hz), 1.02 (d, 3H, J=7.2 Hz), 1.95-2.22 (m, 2H), 2.65 (dq, 1H, J=4.4, 7.2 Hz), 3.05-3.23 (m, 1H), 3.80-4.00 (m, 2H), 4.38-4.47 (m, 1H); $^{13}$C NMR syn (CDCl$_3$) δ=7.58, 12.8, 14.0, 34.6, 49.4, 61.3, 73.0, 173.5, 211.3; anti (C$_6$D$_6$) δ=7.7, 11.0, 14.0, 34.0, 49.5, 61.6, 71.7, 173.7, 209.9; IR (neat) syn 3484, 2981, 2940, 1739, 1716, 1459, 1409, 1375, 1268, 1209, 1108, 1066, 1025, 975, 862, 808, 748; anti 3488, 2981, 2940, 1733, 1716, 1459, 1373, 1218, 1145, 1025, 977, 862, 800, 752 cm$^{-1}$; HRMS (FAB); Exact mass calcd for C$_9$H$_{17}$O$_4$ [M+H]$^+$, 189.1127. Found 189.1120.;

Example 9

A reaction was performed in a same manner as in Example 7 except that an enecarbamate represented by the following formula as an enamide:

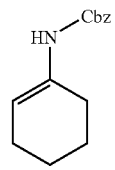

Thus, a next compound was obtained at a yield of 85% with a syn/anti of 16/84 and 94 ee (%).

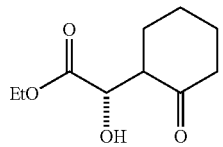

(1S)-Hydroxy-(2-oxo-cyclohexyl)-acetic acid ethyl ester (syn/anti mixture): $^1$H NMR anti((1S, 1'R), tentatively assignment) (C$_6$D$_6$) δ=0.95 (t, 3H, J=7.1 Hz), 0.94-1.20 (m, 2H), 1.30-1.42 (m, 2H), 1.56-1.84 (m, 3H), 2.02-2.12 (m, 1H), 2.60-2.70 (m, 1H), 3.35 (d, 1H, J=7.2 Hz), 3.84 (dd, 1H, J=3.2, 7.2 Hz), 4.02 (dq, 2H, J =1.9, 7.1 Hz); distinguishable syn peaks δ=0.88 (t, 3H, J=7.1Hz), 2.12-2.21 (m, 1H), 2.48-2.57 (m, 1H), 2.94 (d, 1H, J=5.0 Hz), 4.60 (dd, 1H, J=3.2, 5.0 Hz); $^{13}$C NMR anti (CDCl$_3$) δ=14.1, 24.8, 26.9, 30.1, 42.0, 53.7, 61.6, 71.1, 173.4, 211.2; distinguishable syn peaks δ=14.2, 24.6, 27.1, 41.9, 53.8, 61.7, 69.2, 173.6, 210.4; HRMS (FAB); Exact mass calcd for C$_{10}$H$_{17}$O$_4$ [M+H]$^+$, 201.1127. Found 201.1127.;

Example 10

A reaction was performed in a same manner as in Example 7 except that an enamide (2) having an α-substituent as shown in Table 7 was used. The results are also shown in Table 7.

TABLE 7

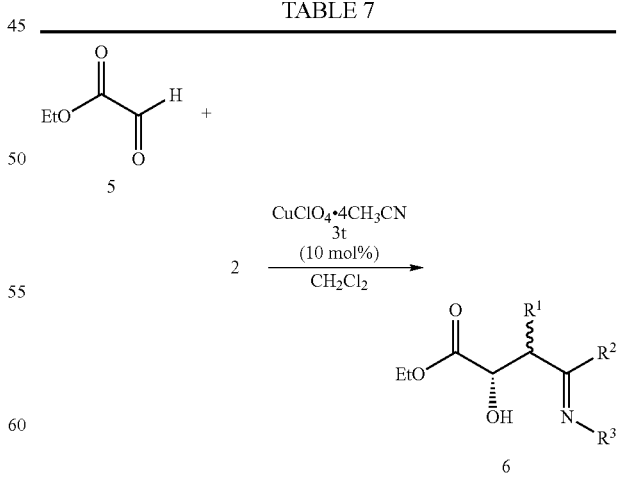

| entry | 2 | product | yield (%)[a] | syn/anti[b] | ee (%)[c] |
|---|---|---|---|---|---|
| 1 | 2fE | 7f | 83 | 1/99 | 98 |
| 2[d] | 2fE[e] | 7f | 93 | 1/99 | 97 |
| 3[d] | 2fE[f] | 7f | 95 | 1/99 | 98 |

TABLE 7-continued

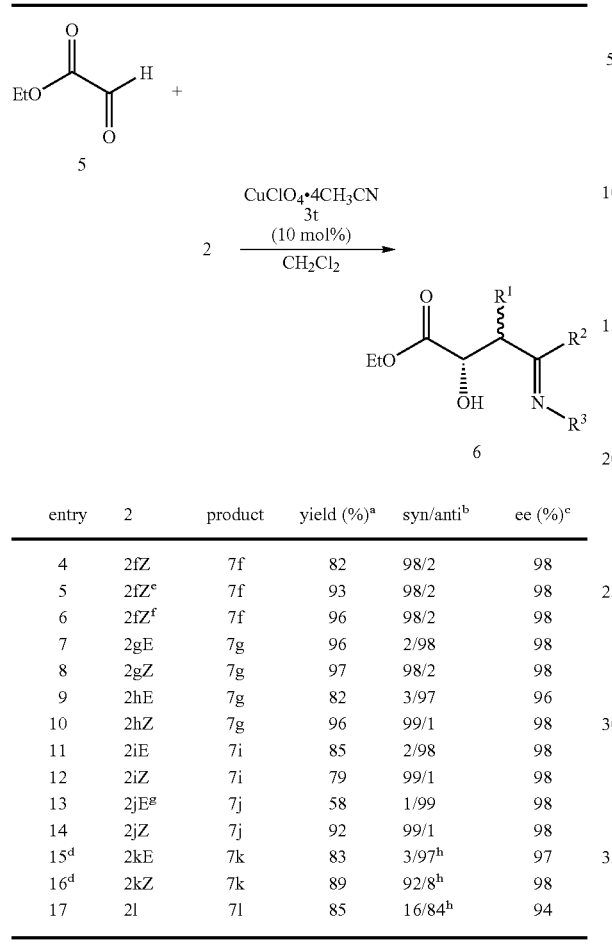

| entry | 2 | product | yield (%)[a] | syn/anti[b] | ee (%)[c] |
|---|---|---|---|---|---|
| 4 | 2fZ | 7f | 82 | 98/2 | 98 |
| 5 | 2fZ[e] | 7f | 93 | 98/2 | 98 |
| 6 | 2fZ[f] | 7f | 96 | 98/2 | 98 |
| 7 | 2gE | 7g | 96 | 2/98 | 98 |
| 8 | 2gZ | 7g | 97 | 98/2 | 98 |
| 9 | 2hE | 7g | 82 | 3/97 | 96 |
| 10 | 2hZ | 7g | 96 | 99/1 | 98 |
| 11 | 2iE | 7i | 85 | 2/98 | 98 |
| 12 | 2iZ | 7i | 79 | 99/1 | 98 |
| 13 | 2jE[g] | 7j | 58 | 1/99 | 98 |
| 14 | 2jZ | 7j | 92 | 99/1 | 98 |
| 15[d] | 2kE | 7k | 83 | 3/97[h] | 97 |
| 16[d] | 2kZ | 7k | 89 | 92/8[h] | 98 |
| 17 | 2l | 7l | 85 | 16/84[h] | 94 |

[a]Isolated yield of ketone product.
[b]Determined by HPLC.
[c]Ee of the major diastereomer, determined by HPLC.
[d]−20° C.
[e]1 mol % of catalyst was used.
[f]0.1 mol % of catalyst was used.
[g]1 (1.0 eq.) and 2 (2.0 eq.) were used.
[h]Determined by NMR analysis.

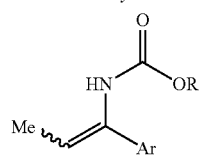

2f: Ar = Ph, R = Bn
2g: Ar = PMP, R = Bn
2h: Ar = PMP, R = Et
2i: Ar = PCP, R = Bn

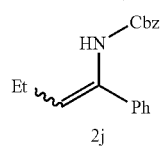

2j

2k

TABLE 7-continued

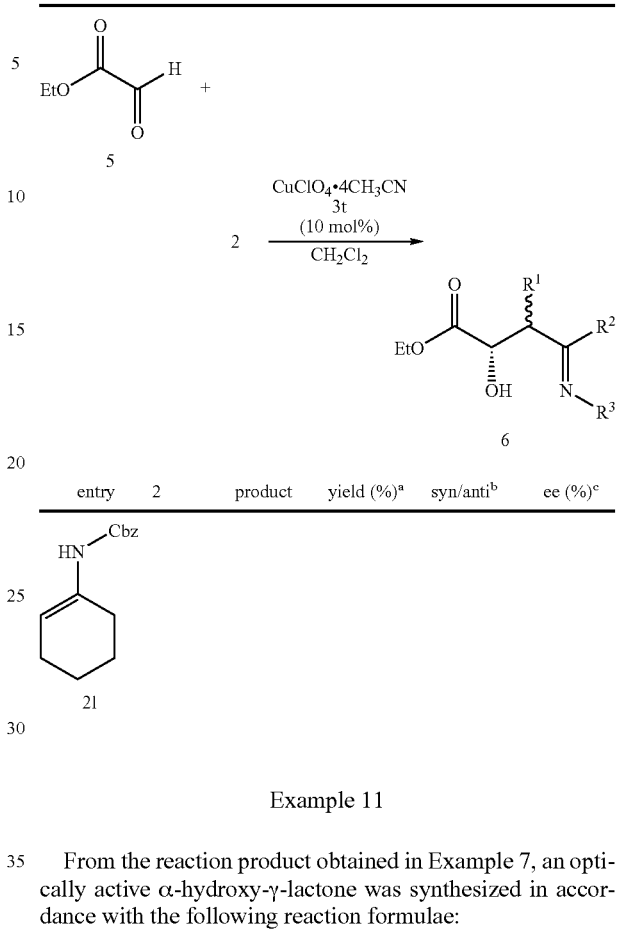

| entry | 2 | product | yield (%)[a] | syn/anti[b] | ee (%)[c] |
|---|---|---|---|---|---|

21

Example 11

From the reaction product obtained in Example 7, an optically active α-hydroxy-γ-lactone was synthesized in accordance with the following reaction formulae:

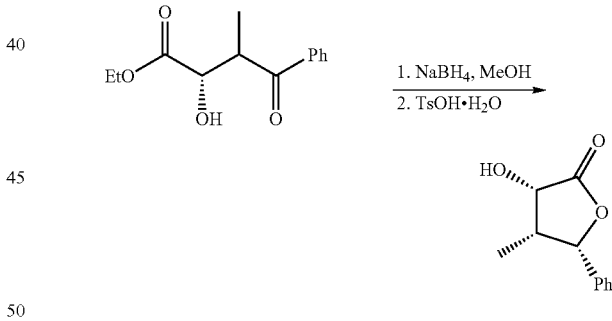

Namely, MeOH (1.0 ml) of the anti-body (45.6 mg, 0.193 mmol) of the reaction product was added with NaBH₄ (14.6 mg, 0.39 mmol) at 0° C., stirred for 10 minutes, added with acetone, stirred further for 5 minutes and, then, added with a saturated aqueous solution of NH₄Cl.

The resultant mixture was subjected to extraction by using CH₂Cl₂, dried and, then, a solvent was evaporated. Thereafter, the resultant CH₂C₂ solution (1 ml) was added with TsOH.H₂O and, then, stirred for 13.5 hours at room temperature.

The resultant reaction product was added with a saturated aqueous solution of NaHCO₃, subjected to extraction by using CH₂Cl₂, dried and, then, subjected to a solvent-evaporation treatment. The resultant crude product was purified by using silica gel chromatography. As a product, the lactone compound as shown in the above-described reaction formulae and all epi-body thereof (ratio: 55/45) were obtained as a diastereomer mixture in an amount of 19.8 mg at a yield of 53%.

Identification values of the products are shown below.

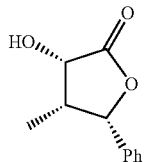

(3S, 4R, 5S)-3-Hydroxy-4-methyl-5-phenyl-dihydro-furan-2-one Mp. 150-151° C.; $^1$H NMR (CDCl$_3$) δ=0.65 (d, 3H, J=7.3 Hz), 2.75 (brs 1H), 2.98-3.08 (m, 1H), 4.79 (d, 1H, J=6.8 Hz), 5.57 (d, 1H, J=4.6 Hz), 7.25-7.30 (m, 2H), 7.30-7.38 (m, 1H), 7.38-7.45 (m, 2H); $^{13}$C NMR (CDCl$_3$) δ=7.4, 41.1, 72.1, 80.2, 125.2, 128.2, 128.6, 135.1, 177.0; IR (neat) 3443, 2963, 1758, 1452, 1414, 1294, 1194, 1148, 1051, 956, 754, 701, 622, 478 cm$^{-1}$; HRMS (FAB); Exact mass calcd for C$_{11}$H$_{13}$O$_3$ [M+H]$^+$, 193.0865. Found 193.0872.;

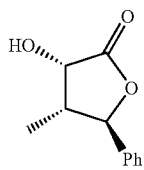

(3S, 4R, 5R)-3-Hydroxy-4-methyl-5-phenyl-dihydro-furan-2-one (epi-): $^1$H NMR (CDCl$_3$) δ=1.22 (d, 3H, J=7.1 Hz), 2.62 (tq, 1H, J=5.1, 6.8 Hz), 2.86 (brs, 1H), 4.47 (d, 1H, J=6.8 Hz), 5.26 (d, 1H, J=5.1 Hz), 7.20-7.45 (m, 5H); $^{13}$C NMR (CDCl$_3$) δ=10.8, 43.2, 69.7, 85.8, 125.3, 128.6, 128.8, 137.7, 176.9; IR (neat) 3430, 3039, 2924, 2857, 1772, 1455, 1275, 1202, 1143, 1093, 986, 889, 805, 742, 702 cm$^{-1}$; HRMS (FAB); Exact mass calcd for C$_{11}$H$_{13}$O$_3$ [M+H]$^+$, 193.0865. Found 193.0864.;

In a same manner as described above, by using the syn-body of the product in Example 7 as a raw material, a lactone compound and an epi-body thereof (ratio: 86/14) were obtained at a yield of 84%.

Identification values of the products are shown below.

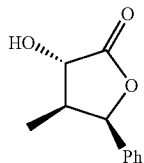

(3S, 4S, 5R)-3-Hydroxy-4-methyl-5-phenyl-dihydro-furan-2-one: $^1$H NMR (CDCl$_3$) δ=0.87 (d, 3H, J=7.0 Hz), 2.70-2.92 (m, 1H), 3.18 (brs, 1H), 4.24 (d, 1H, J=9.9 Hz), 5.63 (d, 1H, J=8.1 Hz), 7.05-7.18 (m, 2H), 7.30-7.45 (m, 3H); $^{13}$C NMR (CDCl$_3$) δ=13.3, 42.1, 72.2, 82.4, 125.7, 128.5, 128.6, 135.5, 177.5; IR (neat) 3362, 2970, 1776, 1455, 1334, 1184, 1145, 1096, 991, 897, 755, 701, 464 cm$^{-1}$; HRMS (FAB); Exact mass calcd for CH$_{11}$H$_{13}$O$_3$ [M+H]$^+$, 193.0865. Found 193.0872.;

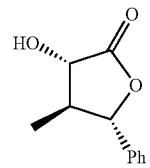

(3S, 4S, 5S)-3-Hydroxy-4-methyl-5-phenyl-dihydro-furan-2-one (epi-): $^1$H NMR (CDCl$_3$) δ=1.24 (d, 3H, J=6.4 Hz), 2.41 (tq, 1H, J=6.4, 10.6 Hz), 3.24 (brs, 1H), 4.25 (d, 1H, J=11.0 Hz), 4.87 (d, 1H, Example 12

A dichloromethane solution (2 ml) of Ni (OTf)$_2$ was added with a dichloromethane solution (3 ml) of chiral diamine (0.15 mmol) represented by the formula shown below in an argon atmosphere at room temperature and, then, stirred for 8 hours. After being cooled to 0° C., the resultant solution was added with a dichloromethane solution (2.5 ml) of diketone (1.5 mmol) and a dichloromethane solution (2.5 ml) of enamide (1.0 mmol) in succession. After being stirred for 48 hours, the resultant mixture was added with a 48% hydrobromic acid solution (0.5 ml) in drops, stirred for 5 minutes and, then, added with a saturated aqueous solution of sodium hydrogen carbonate. The resultant reaction solution was subjected to extraction using dichloromethane and the resultant organic phase was rinsed with water and, then, a saturated saline solution and, thereafter, dried on sodium sulfate anhydride and, then, concentrated under a reduced pressure, to thereby obtain a product of constitution. The thus-obtained product of constitution was purified by using silica gel chromatography, to thereby obtain hydroxydiketone at a yield of 77% with an optical purity of 59% ee.

When a reaction was performed under same conditions as described above except that Cu(OTf)$_2$ was used in place of Ni(OTf)$_2$, hydroxydiketone was obtained at a yield of 52% with an optical purity of 72% ee.

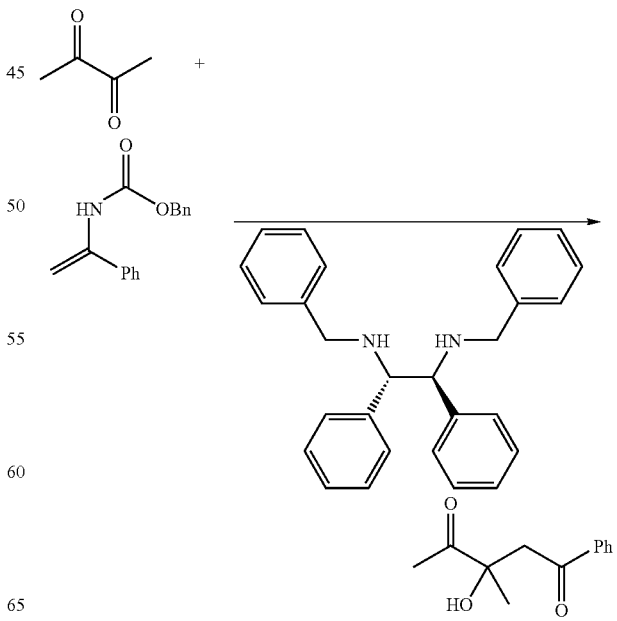

Example 13

A reaction was performed in a same manner as in Example 12, except for using a chiral catalyst system constituted by using Ni(OTf)$_2$ or Cu(OTf)$_2$ and various types of chiral diamine ligands (A, B, C, D, E). The results are shown in Table 8.

TABLE 8

| entry | liganal | metal | yield (%) | ee (%) |
|---|---|---|---|---|
| 1 | A | Ni | 30 | 83 |
| 2 | A | Cu | 70 | 40 |
| 3 | B | Ni | 23 | 70 |
| 4 | B | Cu | 61 | 58 |
| 5 | C | Ni | 24 | 81 |
| 6 | C | Cu | 62 | 33 |
| 7 | D | Ni | 67 | 75 |
| 8 | D | Cu | 70 | 49 |
| 9 | E | Ni | 37 | 80 |
| 10 | E | Cu | 61 | 62 |

10% by mol was used in DCM. Reaction at 0° C.

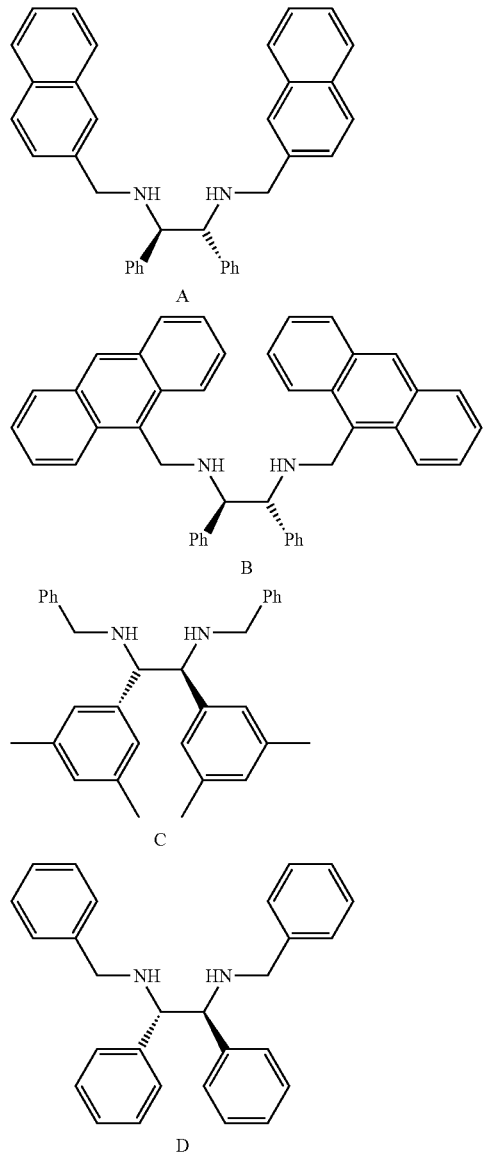

TABLE 8-continued

| entry | liganal | metal | yield (%) | ee (%) |
|---|---|---|---|---|

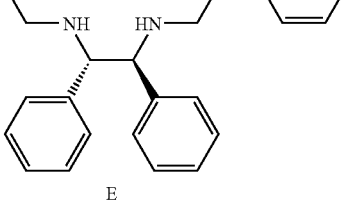

E

Example 14

A reaction was performed in a same manner as in Example 12, except that NiCl$_2$ and AgOTf of two equivalents thereof were used in place of Ni(OTf)$_2$.

As a result, a hydroxydiketone was obtained at a yield of 85% and an optical purity of 57% ee. Further, when AgOTf of three equivalents thereof was used, the yield was 56% and the optical purity was 81% ee.

INDUSTRIAL APPLICABILITY

As has been described above in detail, according to the present invention, there is provided a method of an enantioselective nucleophilic addition reaction to an aldehyde group which enables an asymmetric synthesis of an optically active α-hydroxy-γ-keto acid ester, an optically active α-hydroxy-γ-amino acid ester, an optically active hydroxydiketone or the like which is useful as a raw material or a synthesis intermediate for producing a pharmaceutical preparation, an agricultural chemical, a fragrance, a functional polymer or the like. Then, according to the invention, high stereoselective reaction is made possible and, particularly in the case of an enecarbamate having an α-1 substitution, high diastereoselectivity and enantioselectivity are realized. Further, there is provided a novel method for synthesizing an optically active γ-lactam or any one of γ-lactones.

The invention claimed is:

1. A method of an enantioselective nucleophilic addition reaction of enamide, which is a method of a nucleophilic addition reaction of an enamide compound accompanied by generation of a hydroxyl group (—OH) to a carbonyl group, being characterized by allowing the reaction to be performed in the presence of a chiral catalyst comprising copper or nickel.

2. The method of the enantioselective nucleophilic addition reaction of enamide according to claim 1, being characterized in that the chiral catalyst is constituted by a copper compound or a nickel compound which is a salt of an organic or inorganic acid or a complex or composite of the salt, and a chiral diamine ligand.

3. The method of the enantioselective nucleophilic addition reaction of enamide according to claim 2, being characterized in that the chiral diamine ligand has an ethylene diamine structure as a portion thereof.

4. A method of an enantioselective nucleophilic addition reaction of enamide, which is the method of the enantioselective nucleophilic addition reaction of enamide according to any one of claims 1 to 3, being characterized in that a nucleophilic addition reaction of an enamide compound accompanied by generation of a hydroxyl group (—OH) to a carbonyl group is performed on a compound having a carbonyl group represented by the following formula:

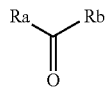

(wherein Ra represents a hydrocarbon group which may have a substituent, $R^0$—CO— or $R^0$—O—CO—, wherein $R^0$ represents a hydrocarbon group which may have a substituent; and Rb represents a hydrogen atom or a hydrocarbon group which may have a substituent).

5. The method of the enantioselective nucleophilic addition reaction of enamide according to claim 4, being characterized in that the compound having the carbonyl group is a glyoxylic acid ester.

6. The method of the enantioselective nucleophilic addition reaction of enamide according to claim 5, being characterized in that the compound having a carbonyl group is a glyoxylic acid ester represented by the following formula (1):

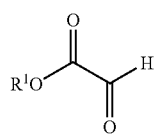

(1)

(wherein $R^1$ represents a hydrocarbon group which may have a substituent; and the enamide compound is represented by the following formula (2):

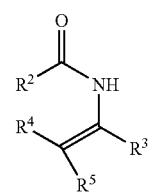

(2)

(wherein $R^2$ represents a hydrocarbon group which may have a substituent or a hydrocarbon group which may have a substituent to be bonded via an oxygen atom;

$R^3$ represents a hydrocarbon group which may have a substituent;

$R^4$ and $R^5$ may be same with or different from each other and each represent a hydrogen atom or a hydrocarbon group which may have a substituent, wherein at least one of them represents a hydrogen atom; and $R^3$ form a ring by being bonded with $R^4$ or $R^5$).

7. A method for synthesizing an optically active α-hydroxy-γ-keto acid ester, being characterized in that, after the nucleophilic addition reaction according to claim 6, an acid treatment is performed, to thereby generate a compound represented by at least one of the following formulae (3):

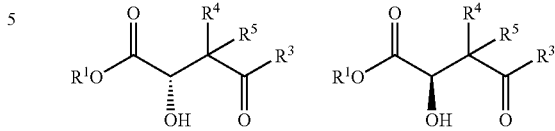

(3)

(wherein $R^1$, $R^3$, $R^4$ and $R^5$ are as defined in claim 6).

8. A method for synthesizing an optically active α-hydroxy-γ-amino acid ester, being characterized in that, after the nucleophilic addition reaction according to claim 6, a reduction treatment is performed, to thereby generate a compound represented by at least one of the following formulae (4):

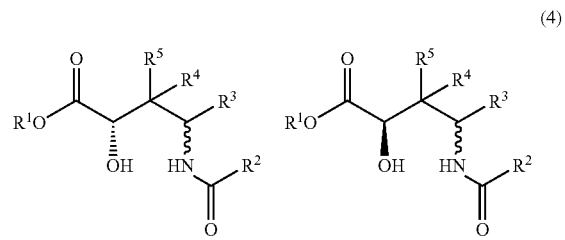

(4)

(wherein $R^1$, $R^2$, $R^3$, $R^4$ and $R^5$ are as defined in claim 6).

9. A method for synthesizing optically active α-hydroxy-γ-lactams, being characterized in that, after a substituent ($R^2$CO—) on a γ-amino group of the optically active α-hydroxy-γ-amino acid ester synthesized by the method according to claim 8 is removed, a cyclization reaction is performed, to thereby generate a compound represented by at least one of the following formulae (5):

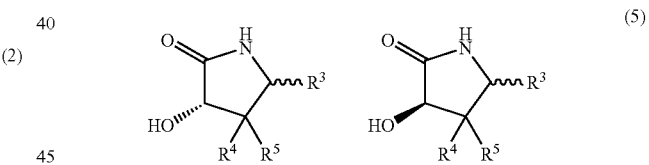

(5)

(wherein $R^3$, $R^4$ and $R^5$ each represent same article as described above).

10. A method for synthesizing any one of optically active α-hydroxy-γ-lactones, being characterized in that the optically active α-hydroxy-γ-keto acid ester synthesized by the method according to claim 7 is subjected to a reduction reaction and, subsequently, to a cyclization reaction, to thereby generate a compound represented by at least one of the following formulae (6):

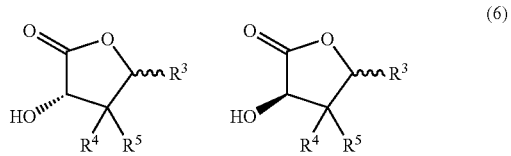

(6)

(wherein $R^3$, $R^4$ and $R^5$ each represent same article as described above).

11. A method of an enantioselective nucleophilic addition reaction of enamide, which is the enantioselective nucleophilic addition reaction of enamide according to claim 4, being characterized in that the compound having the carbonyl group is a diketone compound represented by the following formulae (7):

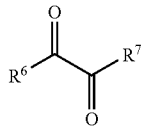

(7)

(wherein $R^6$ and $R^7$ are same with or different from each other and each represent a hydrocarbon group which may have a substituent); and the enamide compound is represented by the following formula (2):

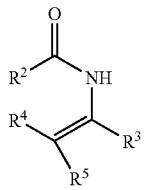

(2)

(wherein $R^2$ represents a hydrocarbon group which may have a substituent or a hydrocarbon group which may have a substituent to be bonded via an oxygen atom;

$R^3$ represents a hydrocarbon group which may have a substituent;

$R^4$ and $R^5$ may be same with or different from each other and each represent a hydrogen atom or a hydrocarbon group which may have a substituent, wherein at least one of them represents a hydrogen atom; and $R^3$ may form a ring by being bonded with $R^4$ or $R^5$).

12. A method for synthesizing an optically active hydroxy-diketone compound, being characterized in that, after the nucleophilic addition reaction according to claim 11, a reduction treatment is performed, to thereby generate an optical active compound represented by the following formula (8):

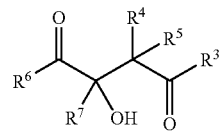

(8)

(wherein $R^6$, $R^7$, $R^3$, $R^4$ and $R^5$ each represent same article as described above).

* * * * *